US012708563B2

(12) United States Patent
Riedel et al.

(10) Patent No.: US 12,708,563 B2
(45) **Date of Patent: *Aug. 18, 2026**

(54) SYSTEM AND METHOD FOR NOMOGRAM-BASED REFRACTIVE LASER SURGERY

(71) Applicant: ALCON INC., Fribourg (CH)

(72) Inventors: Peter Riedel, Nuremberg (DE); Johannes Agethen, Erlangen (DE)

(73) Assignee: Alcon Inc., Fribourg (CH)

(*) Notice: Subject to any disclaimer, the term of this patent is extended or adjusted under 35 U.S.C. 154(b) by 371 days.

This patent is subject to a terminal disclaimer.

(21) Appl. No.: 18/461,358

(22) Filed: Sep. 5, 2023

(65) Prior Publication Data

US 2023/0404804 A1 Dec. 21, 2023

Related U.S. Application Data

(63) Continuation of application No. 16/426,497, filed on May 30, 2019, now Pat. No. 11,883,328.

(60) Provisional application No. 62/678,027, filed on May 30, 2018.

(51) Int. Cl.
*A61F 9/008* (2006.01)

(52) U.S. Cl.
CPC ...... *A61F 9/00804* (2013.01); *A61F 9/00827* (2013.01); *A61F 2009/00859* (2013.01); *A61F 2009/00872* (2013.01)

(58) Field of Classification Search
CPC .............. A61F 9/00804; A61F 9/00827; A61F 2009/00859; A61F 2009/00872
See application file for complete search history.

(56) References Cited

U.S. PATENT DOCUMENTS

| | | | | |
|---|---|---|---|---|
| 2007/0161972 A1* | 7/2007 | Felberg | ............... | A61F 9/00806 351/200 |
| 2009/0187387 A1 | 7/2009 | Bille | | |
| 2015/0134316 A1* | 5/2015 | Dai | ..................... | A61F 9/00804 703/11 |
| 2016/0038276 A1 | 2/2016 | Albertazzi | | |

* cited by examiner

*Primary Examiner* — Carl H Layno
*Assistant Examiner* — Aya Ziad Bakkar

(57) ABSTRACT

The present disclosure provides a refractive laser surgery system including a processor having access to memory media storing instructions or sets of instructions executable by the processor to identify a surgical parameter; correct the surgical parameter based on a nomogram specific for the refractive laser surgery system to provide a nomogram-based corrected surgical parameter; store the surgical parameter and the nomogram-based corrected surgical parameter in the memory media as data for a patient or for one or both eyes of the patient; and compare the surgical parameter and nomogram-based corrected surgical parameter to generate a graphical representation of the surgical parameter, a target outcome parameter associated with the surgical parameter, or both, and the nomogram-based corrected surgical parameter, to generate a warning based on a comparison of the nomogram-based corrected surgical parameter to the surgical parameter or an absolute value, or both. Methods of using the system are also provided.

20 Claims, 2 Drawing Sheets

SYSTEM AND METHOD FOR NOMOGRAM-BASED REFRACTIVE LASER SURGERY

CROSS REFERENCE TO RELATED APPLICATIONS

The present application claims the benefit of priority to U.S. Provisional Application No. 62/678,027, filed on May 30, 2018, and U.S. application Ser. No. 16/426,497, filed on May 30, 2019, now U.S. Pat. No. 11,883,328. The entire disclosures of the foregoing applications are incorporated by reference herein.

TECHNICAL FIELD

The present disclosure provides a system and method for nomogram-based refractive laser surgery, which may be performed on an eye of a patient.

BACKGROUND

When light enters the human eye, it passes through the clear cornea, located in front of the pupil and iris, then through the lens, located internally behind the pupil, then finally to the retina located internally at the back of the eye. Refractive errors may result in the light not being properly focused on the retina, causing, for example, near-sightedness, far-sightedness, or astigmatism. Refractive errors may result from aberrations in the cornea, the lens, or both, but they are often most easily corrected by modifying the cornea, due to is easily-accessible location on the external surface of the eye. Corneal modifications are often carried out using refractive laser surgery. One example of refractive laser surgery is laser-assisted in situ keratomileusis (LASIK), during which a surgeon employs a sophisticated surgical system containing an excimer laser to ablate certain regions of the cornea in a way that corrects refractive errors in the eye. Another example of refractive laser surgery is small incision lenticule extraction (SMILE), during which the surgeon employs a sophisticated femto laser surgical system to photodisrupt portions of the cornea to create a lenticule that is removed, leaving the cornea in a shape that corrects refractive errors in the eye.

SUMMARY

The present disclosure provides a refractive laser surgery system including a processor having access to memory media storing instructions or sets of instructions executable by the processor to identify a surgical parameter; correct the surgical parameter based on a nomogram specific for the refractive laser surgery system to provide a nomogram-based corrected surgical parameter; store the surgical parameter and the nomogram-based corrected surgical parameter in the memory media as data for a patient or for one or both eyes of the patient; and compare the surgical parameter and nomogram-based corrected surgical parameter to generate a graphical representation of the surgical parameter, a target outcome parameter associated with the surgical parameter, or both, and the nomogram-based corrected surgical parameter, to generate a warning based on a comparison of the nomogram-based corrected surgical parameter to the surgical parameter or an absolute value, or both.

The refractive laser surgery system may further include the following additional features, which may be combined with one another in all possible combinations unless clearly mutually exclusive:

i) the nomogram specific for the refractive laser surgery system may be generated using past surgical parameter data, past target outcome parameter data associated with the past surgical parameter data, and past actual outcome parameter data for the refractive laser surgery system;

ii) the system may further include a user interface and the instructions or sets of instructions may be further executable by the processor to cause the user interface to display the graphical representation or convey the warning to a user; and accept an input from the user that verifies the nomogram-based corrected surgical parameter and then allow a refractive laser surgery performed using the refractive laser surgery system to proceed, or accept an input from the user that does not verify the nomogram-based corrected surgical parameter and then not allow the refractive laser surgery to proceed;

iii) the refractive laser surgery system may further include an excimer laser or a femto laser and the instructions or set of instructions may be further executable by the processor to calculate an ablation profile or a photodisruption profile for a cornea of an eye of the patient using the nomogram-based corrected surgical parameter; store the ablation profile or photodisruption profile in the memory media as data for the patient or for one or both eyes of the patient;

compare the ablation profile or photodisruption profile to the surgical parameter to determine if a refractive laser surgery on the cornea of the eye may safely proceed using the ablation profile or photodisruption profile; and if the refractive laser surgery may safely proceed, direct the excimer laser to ablate the cornea in accordance with the ablation profile or direct the femto laser to photodisrupt the cornea in accordance with the photodisruption profile;

iv) the processor may further have access to memory media storing past surgical parameter data, past target outcome parameter data associated with the past surgical parameter data, and past actual outcome parameter data for the refractive laser surgery system, and instructions or sets of instructions may be executable by the processor to create the nomogram specific for the refractive laser surgery system based on all or a set of the past surgical parameter data, past target outcome parameter data associated with the past surgical parameter data, and past actual outcome parameter data for the refractive laser surgery system; and store the nomogram in the memory media;

v) the instructions or set of instructions may be further executable by the processor to compare past surgical parameter data, past target outcome parameter data associated with the past surgical parameter data, and past actual outcome parameter data for the refractive laser surgery system to determine if a systematic deviation occurs between the past target outcome parameter and the past actual outcome parameter based on the past surgical parameter; and if a systematic deviation occurs, create the nomogram for correcting the surgical parameter;

vi) the instructions or set of instructions may be further executable by the processor to create a new nomogram using additional past data if a set time interval has passed;

vii) the system may further include diagnostic equipment, wherein the instructions or set of instructions may be further executable by the processor to cause the diagnostic equipment to determine the surgical parameter, an actual outcome parameter associated with the surgical parameter, or both;

viii) the system may further include a communication interface, and wherein the instructions or set of instructions may be further executable by the processor to, via the communication interface, obtain the surgical parameter, an actual outcome parameter associated with the surgical parameter, or both from diagnostic equipment external to the refractive laser surgery system.

ix) the nomogram may include a correction table, a set of instructions that, when executed by the processor, arrive at a same value as would be obtained when using a correction table, or a function that calculates appropriate corrections.

The present disclosure further provides a method for performing refractive laser surgery on a cornea of an eye of a patient using a refractive laser surgery system including a processor and memory media accessible by the processor and storing instructions or sets of instructions executable by the processor. The method includes identifying a surgical parameter; correcting the surgical parameter based on a nomogram specific for the refractive laser surgery system to provide a corrected surgical parameter; storing the surgical parameter and the corrected surgical parameter in the memory media as data for the patient or for one or both eyes of the patient; and comparing the surgical parameter and corrected surgical parameter to generate a graphical representation of the surgical parameter, a target outcome parameter associated with the surgical parameter, or both, and the nomogram-based corrected surgical parameter, to generate a warning based on a comparison of the nomogram-based corrected surgical parameter to the surgical parameter or an absolute value, or both.

The method may further include the following additional steps, which may be combined with one another in all possible combinations unless clearly mutually exclusive:

i) the nomogram specific for the refractive laser surgery system may be generated using past surgical parameter data, past target outcome parameter data associated with the past surgical parameter data, and past actual outcome parameter data for the refractive laser surgery system;

ii) the method may further include causing a user interface of the refractive laser surgery system to display the graphical representation or convey the warning to a user; and accepting an input from the user that verifies the nomogram-based corrected surgical parameter and then allowing a refractive laser surgery performed using the refractive laser surgery system to proceed, or accepting an input from the user that does not verify the nomogram-based corrected surgical parameter and then not allowing the refractive laser surgery to proceed;

iii) the method may further include calculating an ablation profile or a photodisruption profile for the cornea of the eye of the patient using the nomogram-based corrected surgical parameter; storing the ablation profile or the photodisruption profile in the memory media as data for the patient or for one or both eyes of the patient;

iv) comparing the ablation profile or the photodisruption profile to the surgical parameter to determine if the refractive laser surgery on the cornea of the eye may safely proceed using the ablation profile of the photodisruption profile; and v) if the refractive laser surgery may safely proceed, directing an excimer laser in the refractive laser surgery system to ablate the cornea in accordance with the ablation profile or directing a femto laser in the refractive laser surgery system to photodisrupt the cornea in accordance with the photodisruption profile;

vi) the method may further include creating the nomogram specific for the refractive laser surgery system based on all or a set of past surgical parameter data, past target outcome parameter data associated with the past surgical parameter data, and past actual outcome parameter data for the refractive laser surgery system stored in the memory media; and storing the nomogram in the memory media.

vii) the method may further include comparing past surgical parameter data, past target outcome parameter data associated with the past surgical parameter data, and past actual outcome parameter data for the refractive laser surgery system to determine if a systematic deviation occurs between the past target outcome parameter and the past actual outcome parameter based on the surgical parameter; and if a systematic deviation occurs, creating the nomogram for correcting the surgical parameter;

viii) the method may further include creating a new nomogram using additional past data if a set time interval has passed;

ix) the method may further include determining the surgical parameter, an actual outcome parameter associated with the surgical parameter, or both using diagnostic equipment of the refractive laser surgery system;

x) the method may further include determining the surgical parameter, an actual outcome parameter associated with the surgical parameter, or both using diagnostic equipment external to the refractive laser surgery system; and communicating the surgical parameter, an actual outcome parameter associated with the surgical parameter, or both from the diagnostic equipment to the refractive laser surgery system;

xi) the nomogram may include a correction table, a set of instructions that, when executed by the processor, arrive at a same value as would be obtained when using a correction table, or a function that calculates appropriate corrections.

The above systems and the above methods may be used in all combinations with one another and with all other systems and methods disclosed herein, unless clearly mutually exclusive.

Although the above systems and methods and other systems and methods disclosed herein are described for illustrative purposes in the context of performing a surgery, they may readily be adapted for use during planning of a surgery using a refractive surgical system. In general, during planning stages, if an unacceptable outcome is encountered, rather than a surgical procedure being terminated, the plan for the surgical procedure will be changed to avoid the unacceptable outcome, or, if it is not possible to avoid the unacceptable outcome, the surgery will simply not take place.

BRIEF DESCRIPTION OF THE DRAWINGS

For a more complete understanding of the present disclosure and its features and advantages, reference is now made to the following description, taken in conjunction with the accompanying drawings, in which like numerals represent like elements, and in which.

DETAILED DESCRIPTION

Figure 1:
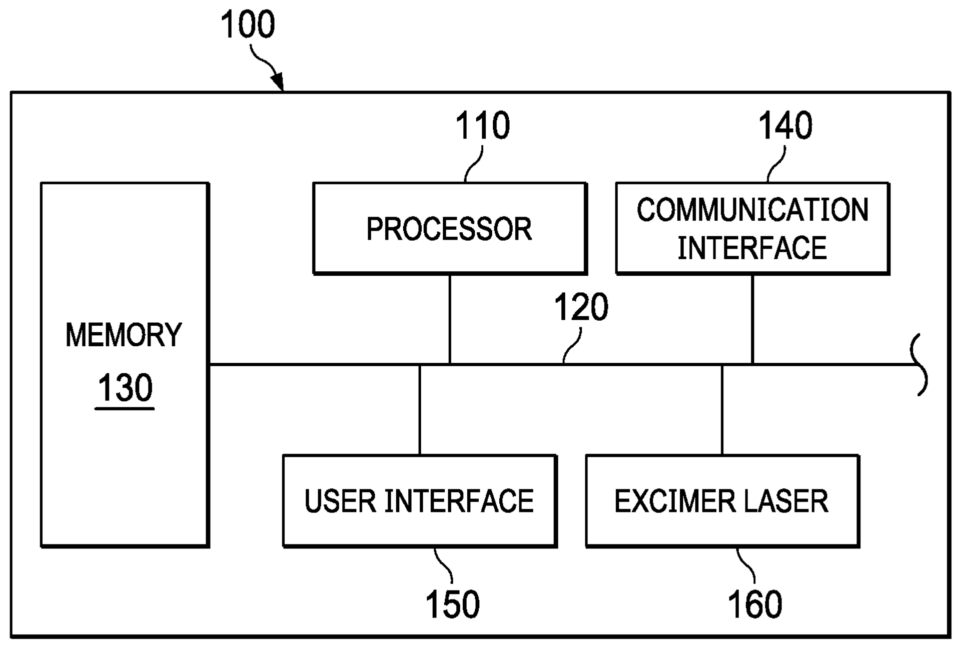
FIG. 1 is a block diagram of selected elements of a refractive laser surgery system.

The present disclosure provides a system and method for nomogram-based refractive laser surgery.

Ophthalmic surgeons often notice consistent deviations from desired refractive laser surgery outcomes based upon the individual refractive laser surgery system used. These deviations are specific for the individual refractive laser surgery system and are often not exhibited across different systems, even when similarly composed and configured. Surgeons frequently collect data on these deviations and use it to develop a nomogram or a set of nomograms for an individual refractive laser surgery system. Surgeons will then reference a nomogram for an individual refractive laser surgery system and use it to correct a surgical parameter, such as a pre-operative measurement of the eye, so that the actual surgical outcome, typically an actual outcome parameter, more closely resembles the precited surgical outcome, typically a target outcome parameter.

For example, the surgeon may determine, based on a nomogram, that in order to obtain a zero refractive error (emmetropia) after refractive surgery using a particular individual system, that for a patient with an actual spherical power of −8.0 Diopter (D), a corrected spherical error of −8.75 D should be entered. Using the same system, for a patient with an actual spherical error of 4.0 D, the corrected spherical error may still be 4.0 D, i.e., no correction of the surgical parameter is needed when the actual spherical power is 4.0 D. However, in a patient with astigmatism with a cylindrical error of −2.0 D, if that same patient has a spherical error of 4.0 D, the surgeon's nomogram may indicate that a corrected spherical error of 4.25 D should be entered when performing surgery with the same laser refractive surgery system in order to obtain a target surgical outcome of a spherical error of zero.

Current practices using nomograms suffer from a number of deficiencies. The conditions during the preoperative examination (e.g. visual acuity test, refraction determination), during the surgical procedure (e.g. microkeratome, flap handling, experience of the surgeon) and the postoperative care are very complex and often lead to fluctuations in the predictability of the treatment result. Also, the entry into patient records in the laser surgery system of a surgical parameter that is not accurate due to a nomogram-based correction.

Accordingly, the present disclosure provides a refractive laser surgery system which may generate nomograms based on actual surgical parameters and actual outcome parameters associated with refractive laser surgery performed with the individual refractive laser surgery system. The refractive laser surgery system may apply these nomograms to correct a surgical parameter when instructed to do so by the user and change other surgical parameters based on the nomogram-based corrected surgical parameter, if appropriate. The refractive laser surgery system may then store the actual surgical parameters along with any nomogram-based corrected surgical parameter in a file in which they are associated, typically a patient file or a file corresponding to one eye of the patient. The refractive laser surgery system may also provide a visual report of deviations in the nomogram-based corrected surgical parameter due to the nomogram-based correction, provide a warning if the deviations are more than a certain percentage of the original parameters or exceed absolute values, or both. Such a report may be provided after surgical parameters are entered into the system, but before surgery, or the plausibility of surgical parameters or nomogram-based corrected surgical parameters may be automatically checked while the surgical parameters are entered and, for example, prevent the entry of surgical parameters that are not plausible.

Such a refractive laser surgery system may also generate additional nomograms representative of actual surgical outcomes obtained with the individual refractive laser surgery system that further correct surgical parameters based on other factors, such as patient age or how eye measurements were obtained.

A laser surgery system as described herein may automatically apply a nomogram-based corrected surgical parameter or wherever the nomogram-based corrected surgical parameter is used by the refractive laser surgery system, eliminating the possibility of user input error. Such a system may first require that a user accept the nomogram-based corrected surgical parameter.

Furthermore, such a refractive laser surgery system may self-update nomograms for that individual system, self-check to see if additional nomograms may be generated, or both. Such self-updates, self-checks, or both may occur in response to a user command or at certain time intervals, such as monthly, weekly, or daily, or even after every use of the refractive laser surgery system to perform refractive laser surgery on a patient or on an eye. Self-updates and self-checks may allow correction for any additional deviations from expected system operations over time. The system may require that a user accept any self-updated nomograms or any new nomograms generated in a self-check before they are implemented in refractive laser surgery.

Accordingly, the present disclosure provides a refractive laser surgery system such as the refractive laser surgery system 100 of FIG. 1. A refractive laser surgery system according to the disclosure may include all of the elements of FIG. 1, but need not necessarily do so. A refractive laser surgery system may include any combinations of less than all of the elements represented in FIG. 1. In addition, any refractive laser surgery system may include additional elements not represented in FIG. 1, including, for example, a femto laser in addition to an excimer laser, a patient bed, or diagnostic equipment.

The refractive laser surgery system 100 of FIG. 1, represented in block diagram form, includes a processor 110 coupled via a shared bus 120 to memory media collectively identified as the memory 130 and having access to such memory media. The refractive laser surgery system 100 further includes a communication interface 140 and a user interface 150, as well as an excimer laser 160. In an alternative embodiment not depicted in FIG. 1, the excimer laser 160 may be replaced with a femto laser.

The processor 110 may be operable to execute instructions or sets of instructions stored in the memory 130 to perform steps of a refractory laser surgery recited herein that are not directly performed by a user. For example, the processor 110 may be operable to generate a nomogram, to use a target outcome parameter and a nomogram to generate a nomogram-based corrected surgical parameter, to use a nomogram-based corrected surgical parameter to further change another surgical parameter, to calculate an ablation profile or photodisruption profile, to control corneal ablation by the excimer laser in accordance with the ablation profile, or to control corneal photodisruption by the femto laser in accordance with the photodisruption profile, to access information stored in the memory 130 via shared bus 120 or to cause information to be stored in the memory 130, and to perform any combinations of any of these functions.

The memory 130 may include persistent media, volatile media, or both, fixed media, removable media, or both, and magnetic media, semiconductor media, or both. Memory 130 is operable to store instructions, data, or both. The memory 130 as shown includes sets or sequences of instructions, namely an operating system 170, a nomogram calculator 180, and a nomogram-based correction calculator 190.

The operating system 170 may be UNIX or UNIX-like operating system, a WINDOWS® (Microsoft Corporation, Washington, US) family operating system, or another suitable operating system.

The nomogram calculator 180 may perform any of the various methods and calculations described herein, optionally combined with methods and calculations known in the art, to generate or update a nomogram specific for the individual refractive laser surgery system 100 and to store such a nomogram in the memory 130.

The nomogram-based correction calculator 190 may perform any of the various methods and calculations described herein, optionally combined with methods and calculations known in the art, to correct a surgical parameter based on a nomogram or change another surgical parameter based on a nomogram-based corrected surgical parameter.

The nomogram-based correction calculator 190 may further perform any of the various methods and calculations described herein, optionally combined with methods and calculations known in the art, to generate a comparative graph showing a surgical parameter and its nomogram-based corrected surgical parameter.

The nomogram-based corrected calculator 190 may further perform any of the various methods and calculations described herein, optionally combined with methods and calculations known in the art, to compare a nomogram-based corrected surgical parameter to an original surgical parameter or a set absolute value, and to generate a warning related to the nomogram-based corrected surgical parameter.

The nomogram-based correction calculator 190 may also perform any of the various methods and calculations described herein, optionally combined with methods and calculations known in the art, to display or communicate to a user information regarding a comparison of a surgical parameter and a nomogram-based corrected surgical parameter, the absolute value of a nomogram-based corrected surgical parameter, or any warnings.

The memory 130 may also include sets or sequences of instructions in the form of a patient data resource (not shown). The patient data resource may store patient data including surgical parameter and outcome parameter data for the patient or for one or both eyes of the patient. The patient data resource may also perform any of the various methods and calculations described herein, optionally combined with methods and calculations known in the art, to access or update patient data, store information regarding a surgical parameter and nomogram-based corrected surgical parameter, and otherwise to perform any of the various methods and calculations described herein, optionally combined with methods and calculations known in the art, for using, updating, and storing patient data.

The memory 130 may further include sets or sequences of instructions in the form of an ablation tool or photodisruption tool (not shown). The ablation tool or photodisruption tool may perform any of the various methods and calculations described herein, optionally combined with methods and calculations known in the art, to generate an ablation profile or a photodisruption profile using at a nomogram-based corrected surgical parameter. The ablation tool or photodisruption tool may further perform any of the various methods and calculations described herein, optionally combined with methods and calculations known in the art, to control the excimer laser 160 to ablate a cornea according to the ablation profile, or to control a femto laser to photodisrupt a cornea according to the photodisruption profile.

The communication interface 140 may be connected to the processor 110, the memory 130, or both via the shared bus 120. The communication interface 140 may be operable to allow the refractive laser surgery system 100 to connect to a network (not shown in FIG. 1) or to other equipment, such as diagnostic equipment, particularly a wavefront determination apparatus.

The user interface 150 may be connected to the processor 110, the memory 130, or both via the shared bus 120. The user interface 150 may be operable to accept commands from a user and to display information to a user. Commands may be input via a keyboard, mouse, touchpad, microphone, voice recognition interface, foot pedal, or other input devices, which may be part of the user interface 150. Information may be displayed on one or more screens, a head up display, or using other display devices, which may be part of the user interface 150. The user interface 150 may further be operable to convey information, such as a warning, to a user using other devices, such as a speaker, light, or buzzer, which may also be part of the user interface 150.

The excimer laser 160 or the femto laser may be connected to the processor 110, the memory 130, or both via the shared bus 120. The excimer laser 160 may be operable to ablate a portion of the cornea in accordance with an ablation profile to correct refractive errors in the eye. The femto laser may be operable to photodisrupt a portion of the cornea in accordance with a photodisruption profile to correct refractive errors in the eye.

Figure 2:
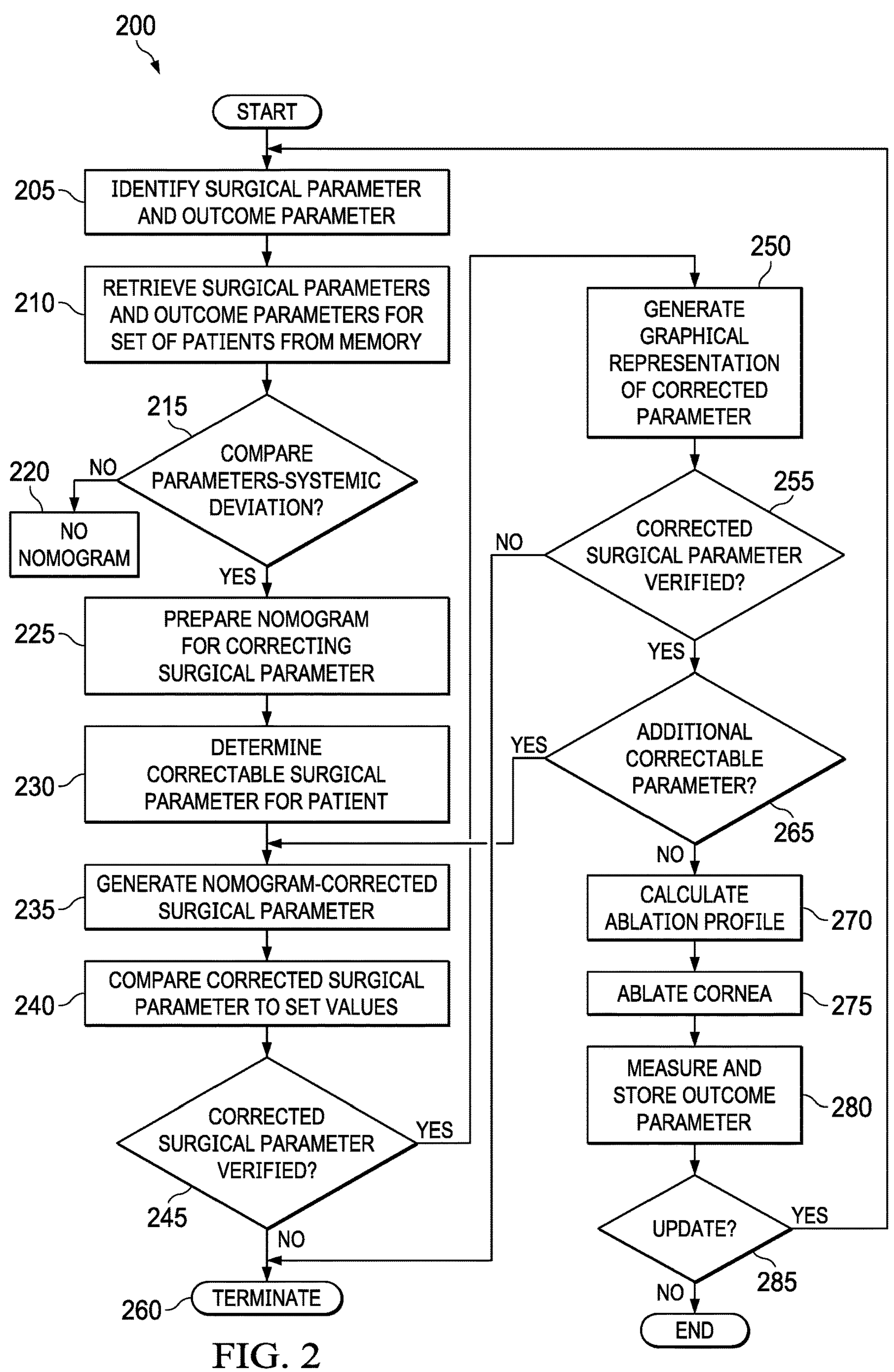
FIG. 2 is a flow chart of selected elements of a method of planning or performing refractive laser surgery using a nomogram.

The present disclosure further provides a method of performing refractive laser surgery, such as the refractive laser surgery method 200 of FIG. 2. The above refractive laser surgery system 100 may implement all or part of the steps of the method not implemented by a user. The method may be implemented by a user controlling a refractive laser surgery system, such as refractive laser surgery system 100. A refractive laser surgery method according to the disclosure may include all of the steps of FIG. 2, but need not necessarily do so. A refractive laser surgery method may include any combinations of less than all of the steps represented in FIG. 2, provided that the steps are implemented in a workable order. Certain steps or combinations of steps, such a generating a nomogram and correcting a surgical parameter based on the nomogram, may be implemented entirely by the laser surgery system without the need for user input beyond an optional start command. In addition, any refractive laser surgery method may include additional steps not represented in FIG. 2, including, for example, cutting a flap in the cornea using a femto laser prior to corneal ablation using an excimer laser, or removing a lenticule after photodisruption with a femto laser.

All refractive laser surgery method steps described herein may also be implemented as a use of all refractive laser surgery systems described herein.

In the refractive laser surgery method 200, in step 205, a surgical parameter and an outcome parameter are identified.

The surgical parameter may be a measured property of the eye on which surgery will be performed, such as spherical power or, for a patient with astigmatism, cylindrical power and the axis for cylinder position, a physical fact about the patient, such as age or history or prior corneal surgery, a setting of the refractive laser surgery system, such as the type of refractive surgery selected, other surgical steps and devices, such as whether a microkeratome or femtosecond laser is used to cut a flap in the cornea, or a surgical environmental condition, such as the temperature of the room where surgery is performed or the time of day.

The outcome parameter is the value of a measured property of the eye as a surgical outcome after a refractive laser surgery is performed. The outcome parameter, for example, may be the optical zone, spherical power or, for a patient with astigmatism, cylindrical power and the axis for cylinder position. The outcome parameter has a target outcome parameter value, which is the value that was used in conjunction with instructions or sets of instructions of the refractive laser surgery machine to determine how to perform the refractive laser surgery. The outcome parameter also has an actual outcome parameter value, which is the value measured in the eye after refractive laser surgery. The actual outcome parameter value may be measured at any medically accepted time after the refractive laser surgery for that parameter, including immediately after the refractive laser surgery, one week after the refractive laser surgery, one month after the refractive laser surgery, or three months after the refractive laser surgery.

The outcome parameter may be the same as the surgical parameter. For example, they may both be the spherical power of the eye.

More than one surgical parameter may be identified, particularly if the surgical parameters are known to sometimes affect one another or jointly affect the outcome parameter. For example, in a patient with astigmatism, both the spherical power and the cylindrical power may be identified as surgical parameters because a spherical power at one cylindrical power may tend to cause one surgical outcome, while the same spherical power at another cylindrical power may tend to cause a different surgical outcome.

Similarly, more than one outcome parameter may be identified, particularly if one surgical parameter may affect multiple outcome parameters.

In some instances, both more than one surgical parameter and more than one outcome parameter may be identified. The method steps are described herein, in most instances, for the sake of simplicity, are described as using one surgical parameter and one outcome parameter. However, the same steps may be performed in a like manner with more than one surgical parameter, more than one outcome parameter, or more than one of both.

The surgical parameter, outcome parameter, or both may be identified by a user, or automatically identified by the refractive laser surgery system. For example, a refractive laser surgery system may simply iteratively identify all possible combinations of surgical parameters, output parameters, or both, or it may identify all logically grouped possible combinations, such as all of those for which data is available for a particular type of surgery. This identification process may be performed as part of a self-check process, which may be initiated by the user or which may occur automatically after set time intervals or after each patient or use of the refractive laser surgery system.

Next, in step 210, the past surgical parameter data and past outcome parameter data for a set of patients is retrieved from the memory of the refractive laser surgery system. The set of patients may be a set selected by a user, or it may be all prior patients, or all prior patients in a particular group, such as all prior patients having a particular type of refractive laser surgery, all prior patients in an age range, or all prior patients who have or have not had previous corneal surgery.

In step 215, the past surgical parameter data and the past target outcome parameter data and past actual outcome parameter data associated with the past surgical parameter data (i.e. for the same patient or the same eye of the same patient) are compared to determine if a systematic deviation has occurred in the past between the target outcome parameter and the actual outcome parameter based on the surgical parameter.

In step 220, if a systematic deviation does not occur, then no nomogram is prepared and the surgical parameter is not corrected. The memory of the refractive laser surgery system may be updated to reflect that no correction is needed for the surgical parameter.

In step 225, if a systematic deviation does occur, then a nomogram is created for correcting the surgical parameter. The nomogram may in the form of a correction table, a set of instructions that, when executed by a processor, arrive at the same value as would be obtained when using a correction table, or a function that calculates appropriate corrections. The memory of the refractive laser surgery system may be updated to contain the nomogram, reflect that a nomogram-based correction to the surgical parameter may be needed, and to contain instructions or a set of instruction for nomogram-based correction of the surgical parameter.

For example, the nomogram may be created by calculating a distribution of a target outcome parameter and an actual outcome parameter of a difference between the target outcome parameter and the actual outcome parameter for a set of refractive laser surgeries as a function of a surgical parameter. A trend line may be calculated for the distribution. For example, a minimum-least-squares error fit trend line may be calculated. The trend line may be used to determine a statistically-based correction to apply to a surgical parameter to achieve an actual outcome parameter that is the same as or within an acceptable variation from a target outcome parameter.

In some more sophisticated nomograms, a confidence level for the distribution may also be set and used to calculate a confidence interval, which may determine whether a nomogram-based correction is applied to a surgical parameter and the degree of nomogram-based correction. In general, if the confidence interval is lower, then a lower amount of nomogram-based correction may be applied than if the confidence interval is higher.

In step 230, a surgical parameter subject to nomogram-based correction is determined for a patient who will undergo refractive laser surgery and stored in the memory of the refractive laser surgery system as data for the patient. The surgical parameter may, for example, be determined using separate diagnostic equipment, which may communicate the information to the refractive laser surgery system via a communication interface, be determined using separate diagnostic equipment and entered into the refractive laser surgery system via a user interface, or be determined using diagnostic equipment that is part of the refractive laser surgery system. A target outcome parameter is also determined for the patient and stored in the memory of the refractive surgery system as data for the patient. The target outcome parameter may be a default outcome parameter for the type of refractive laser surgery, it may be recommended based on calculations made by the refractive laser surgery system, or it may be entered by the user via the user interface.

In step 235, the processor in the refractive laser surgery system compares the surgical parameter, the target outcome parameter, or both to the nomogram and generates a nomogram-based corrected surgical parameter that is entered into the memory of the refractive laser surgery system as data for the patient. The nomogram-based corrected surgical parameter may be the same as the surgical parameter, i.e. no change may be made to its value, if nomogram so dictates.

In step 240, the processor in the refractive laser surgery system compares the nomogram-based corrected surgical parameter to an absolute value and, if the nomogram-based corrected surgical parameter is lower or higher than the absolute value, generates a warning or terminates the refractive laser surgery, or the processor compares the nomogram-based corrected surgical parameter to the surgical parameter and, if the nomogram-based corrected surgical parameter varies from the surgical parameter more than a set amount, such as set percentage that is higher, or lower, or either, generates a warning or terminates the refractive laser surgery.

In step 245, the user is given the option to verify the nomogram-based corrected surgical parameter, for example via the user interface of the refractive laser surgery system. If the user does verify the nomogram-based corrected surgical procedure, then the surgery proceeds. If the user does not verify the nomogram based-corrected surgical procedure, then the surgery is terminated in step 260.

In step 250, the processor in the refractive laser surgery system generates a graphical representation of the surgical parameter, the outcome parameter, or both and the nomogram-based corrected surgical parameter. This graphical representation may be shown via the user interface. The graphical representation may be two dimensional or three dimensional and may include a single graph or a set of graphs, for example representing variation of one surgical parameter, such as spherical power, at different values of a second surgical parameter, such as cylindrical power.

In step 255, the user is given the option to verify the nomogram-based corrected surgical parameter, for example via the user interface of the refractive laser surgery system. If the user does verify the nomogram-based corrected surgical procedure, then the surgery proceeds. If the user does not verify the nomogram based-corrected surgical procedure, then the surgery is terminated in step 260. In alternative methods, the nomogram-based corrected surgical parameter need not be verified. In addition, either verified or non-verified nomogram-based corrected surgical parameters may be used in surgical planning, in which case rather than the surgery being terminated, it would simply not be initiated using the nomogram-based corrected surgical parameters.

Steps 240 and 250 may occur in the same process step or at the same time, so that any warning and graphical representation are presented to the user simultaneously. Steps 245 and 255 may also occur in the same process step or at the same time, so that any verification of the nomogram-based corrected surgical parameter occurs after the user has been presented with both any warnings and the graphical representation.

In step 265, the refractive laser surgery system, automatically or in response to a user input, determines if and additional surgical parameter subject to nomogram-based correction is present. If such an additional parameter is present, then steps 235 through 255 are repeated for that parameter. If no such additional parameter is present, then the refractive laser surgery system proceeds to step 270.

In step 270, an ablation profile or photodisruption profile is calculated by the processor using at least one nomogram-based corrected surgical parameter and stored in the memory of the refractive laser surgery system as data for the patient.

The ablation profile or photodisruption profile, although calculated using a nomogram-based corrected surgical parameter, may also is compared to safety-determinative surgical parameter to determine if the surgery may safely proceed. The safety-determinative surgical parameter may be the same surgical parameter as the nomogram-based corrected surgical parameter, or it may be a different surgical parameter. Example safety-determinative surgical parameters include stromal thickness and maximum ablation depth, which may be used, along with the ablation profile, to determine residual stromal thickness. If the comparison indicates that the surgery is safe to proceed and, optionally, if such determination is confirmed by a user, then the surgery proceeds. If the comparison indicates that the surgery is not safe to proceed or, optionally, if such determination is not confirmed by a user, then the refractive laser surgery terminates in step 260.

This step, in which the ablation profile or photodisruption profile is compared to actual surgical parameters and not to nomogram-corrected surgical parameters is not possible with refractory laser surgery methods in which only a nomogram-corrected surgical parameter is provides to the refractory laser surgery system. It represents a way in which patient safety is improved by having the actual surgical parameters available in the refractory laser surgery system.

In step 275, the processor uses the ablation profile to direct the excimer laser to ablate the cornea of the patient's eye in accordance with the ablation profile, to correct a refractive error in the patient's eye, or the processor uses the photodisruption profile to direct the femto laser to photodisrupt the cornea of the patient's eye in accordance with the photodisruption profile, to correct a refractive error in the patient's eye.

In step 280, an outcome parameter is measured and stored in the memory of the refractive laser surgery system as data for the patient. The outcome parameter, like the surgical parameter, may be measured by diagnostic equipment that is external to or part of the refractive laser surgery system and, if needed may be communicated to the refractive laser surgery system via the communication interface or the user interface.

The outcome parameter may be measured at a selected time after the refractive laser surgery and may be measured more than once.

In step 285, the refractive laser surgery system determines if a set time interval has passed or if a self-check or self-update user input has been received. The set time interval may be monthly, weekly, or daily, or even after every use of the refractive laser surgery system to perform refractive laser surgery on a patient or on an eye. If the set time interval has passed or if a self-check or self-update user input has been received, the method may return to step 205. If not, the method may end.

Alternative methods include those in which one or more nomograms are entered into the memory of the refractive laser surgery system and used as described in steps 230 through 285. Such methods may generate additional nomograms using steps 205 through 225, or they may rely solely on the entered nomograms.

Common subsets of steps of the above method, which may be implemented in isolation, include steps 205 through 255, steps 230 through 285, steps 230 through 265, or steps 270 through 280.

The invention claimed is:

1. A system for updating a nomogram, the system comprising:

memory media storing instructions or sets of instructions executable by a processor; and the processor having access to the memory media storing the instructions or sets of instructions executable by the processor to:

identify a surgical parameter;

correct the surgical parameter based on a nomogram specific for a laser surgery system to provide a nomogram-based corrected surgical parameter, the nomogram based on actual surgical parameters and actual outcome parameters;

store the surgical parameter and the nomogram-based corrected surgical parameter in the memory media as data for a patient or for one or both eyes of the patient;

store the nomogram in the memory media;

compare the surgical parameter and the nomogram-based corrected surgical parameter to generate a graphical representation of the surgical parameter, a target outcome parameter associated with the surgical parameter, or both, and the nomogram-based corrected surgical parameter, to generate a warning based on the comparison of the nomogram-based corrected surgical parameter to the surgical parameter; and periodically update the nomogram based on subsequent actual surgical parameters and subsequent actual outcome parameters.

2. The system of claim 1, wherein the nomogram specific for the laser surgery system is generated using past surgical parameter data, past target outcome parameter data associated with the past surgical parameter data, and past actual outcome parameter data for the laser surgery system.

3. The system of claim 1, wherein the system further comprises a user interface and the instructions or sets of instructions are further executable by the processor to:

cause the user interface to display the graphical representation or convey the warning to a user;

in response to receiving an input from the user that verifies the nomogram-based corrected surgical parameter, allow a laser surgery performed using the laser surgery system to proceed; and in response to receiving an input from the user that does not verify the nomogram-based corrected surgical parameter, not allow the laser surgery to proceed.

4. The system of claim 1, wherein the processor further has access to the memory media storing:

past surgical parameter data, past target outcome parameter data associated with the past surgical parameter data, and past actual outcome parameter data for the laser surgery system; and instructions or sets of instructions are executable by the processor to:

create the nomogram specific for the laser surgery system based on all or a set of the past surgical parameter data, past target outcome parameter data associated with the past surgical parameter data, and past actual outcome parameter data for the laser surgery system; and store the nomogram in the memory media.

5. The system of claim 4, wherein the instructions or set of instructions are further executable by the processor to:

compare the past surgical parameter data, past target outcome parameter data associated with the past surgical parameter data, and past actual outcome parameter data for the laser surgery system to determine if a systematic deviation occurs between the past target outcome parameter and the past actual outcome parameter based on the past surgical parameter; and if a systematic deviation occurs, create the nomogram for correcting the surgical parameter.

6. The system of claim 4, wherein the instructions or set of instructions are further executable by the processor to create a new nomogram using additional past data if a set time interval has passed.

7. The system of claim 1, further comprising diagnostic equipment, wherein the instructions or set of instructions are further executable by the processor to cause the diagnostic equipment to determine the surgical parameter, an actual outcome parameter associated with the surgical parameter, or both.

8. The system of claim 1, wherein:

the laser surgery system further comprises a communication interface; and the instructions or set of instructions are further executable by the processor to, via the communication interface, obtain the surgical parameter, an actual outcome parameter associated with the surgical parameter, or both from diagnostic equipment external to the laser surgery system.

9. The system of claim 1, wherein the nomogram comprises: a correction table; a set of instructions that, when executed by the processor, arrive at a same value as would be obtained when using a correction table; or a function that calculates appropriate corrections.

10. The system of claim 1, wherein the instructions or set of instructions are further executable by the processor to:

calculate an ablation profile or a photodisruption profile for a cornea of an eye of the patient using the nomogram-based corrected surgical parameter;

store the ablation profile or photodisruption profile in the memory media as data for the patient or for one or both eyes of the patient; and compare the ablation profile or photodisruption profile to the surgical parameter to determine if a refractive laser surgery on the cornea of the eye may safely proceed using the ablation profile or photodisruption profile.

11. A method for updating a nomogram for a laser surgery system comprising:

accessing, by a processor, memory media storing instructions or sets of instructions executable by the processor;

identifying, by the processor, a surgical parameter;

correcting, by the processor, the surgical parameter based on a nomogram specific for the laser surgery system to provide a corrected surgical parameter, the nomogram based on actual surgical parameters and actual outcome parameters;

storing, by the processor, the surgical parameter and the corrected surgical parameter in the memory media as data for a patient or for one or both eyes of the patient;

storing, by the processor, the nomogram in the memory media;

periodically updating, by the processor, the nomogram based on subsequent actual surgical parameters and subsequent actual outcome parameters; and comparing, by the processor, the surgical parameter and corrected surgical parameter to generate a graphical representation of the surgical parameter, a target outcome parameter associated with the surgical parameter, or both, and the nomogram-based corrected surgical parameter, to generate a warning based on a comparison of the nomogram-based corrected surgical parameter to the surgical parameter; and sending, by the processor, instructions to the laser surgery system configured to perform a laser surgery on the patient.

12. The method of claim 11, wherein the nomogram specific for the laser surgery system is generated using past surgical parameter data, past target outcome parameter data associated with the past surgical parameter data, and past actual outcome parameter data for the laser surgery system.

13. The method of claim 11, wherein the method further comprises:

causing a user interface of the laser surgery system to display the graphical representation or convey the warning to a user; and accepting an input from the user that verifies the nomogram-based corrected surgical parameter and then allowing a refractive laser surgery performed using the laser surgery system to proceed, or accepting an input from the user that does not verify the nomogram-based corrected surgical parameter and then not allowing the laser surgery to proceed.

14. The method of claim 11, wherein the method further comprises:

calculating, by the processor, an ablation profile or photodisruption profile for the cornea of the eye of the patient using the nomogram-based corrected surgical parameter; and sending, by the processor, instructions to a laser surgery system to perform the laser surgery according to the ablation profile or photodisruption profile.

15. The method of claim 11, wherein the method further comprises:

creating the nomogram specific for the laser surgery system based on all or a set of past surgical parameter data, past target outcome parameter data associated with the past surgical parameter data, and past actual outcome parameter data for the laser surgery system stored in the memory media; and storing the nomogram in the memory media.

16. The method of claim 11, wherein the method further comprises:

comparing past surgical parameter data, past target outcome parameter data associated with the past surgical parameter data, and past actual outcome parameter data for the laser surgery system to determine if a systematic deviation occurs between the past target outcome parameter and the past actual outcome parameter based on the surgical parameter; and if a systematic deviation occurs, creating the nomogram for correcting the surgical parameter.

17. The method of claim 16, wherein the method further comprises creating a new nomogram using additional past data if a set time interval has passed.

18. The method of claim 11, wherein the method further comprises determining the surgical parameter, an actual outcome parameter associated with the surgical parameter, or both using diagnostic equipment of the laser surgery system.

19. The method of claim 11, wherein the method further comprises:

determining the surgical parameter, an actual outcome parameter associated with the surgical parameter, or both using diagnostic equipment external to the laser surgery system; and communicating the surgical parameter, the actual outcome parameter associated with the surgical parameter, or both from the diagnostic equipment to the laser surgery system.

20. The method of claim 11, wherein the nomogram comprises: a correction table; a set of instructions that, when executed by the processor, arrive at a same value as would be obtained when using a correction table; or a function that calculates appropriate corrections.

* * * * *